United States Patent [19]

Comb et al.

[11] Patent Number: 5,210,036

[45] Date of Patent: May 11, 1993

[54] PURIFIED THERMOSTABLE DNA POLYMERASE OBTAINABLE FROM THERMOCOCCUS LITORALIS

[75] Inventors: Donald G. Comb, Beverly; Rebecca B. Kucera, Beverly, both of Mass.

[73] Assignee: New England Biolabs, Inc., Beverly, Mass.

[21] Appl. No.: 513,994

[22] Filed: Apr. 26, 1990

[51] Int. Cl.$^5$ .......................... C12N 9/12; C12N 9/10
[52] U.S. Cl. ..................................... 435/194; 435/193
[58] Field of Search .............................. 435/193, 194

[56] References Cited

U.S. PATENT DOCUMENTS 4,889,818 12/1989 Gelfand et al. .................... 435/194

OTHER PUBLICATIONS

Rüttimann et al. (1985) *Eur. J. Biochem.*, 149, 41–46.
Bechtereva et al. (1989) *Nucleic Acid Res.*, 17(24), 10507.
Elie et al. (1989) *Eur. J. Biochem.*, 178, 619–626.
Saiki et al. (1988) *Science*, 239, 487–491.
Brock (1985) *Science*, 230, 132–138.
Hamel, European Journal of Biochemistry, 190:517–521 (1990).
Klimczak, et al., Nucleic Acids Research, 13(14): 5269–5282 (1985).
Salhi, et al., Biochemical and Biophysical Research Communications, 167(3): 1341–1347 (1990).
Salhi, et al., Journal of Molecular Biology, 209:635–644 (1989).
Klimczak, et al., Biochemistry, 25:4850–4855 (1986).
Belkin, et al., Arch. Microbiology, 141:181–186 (1985).
Bessman, et al., J. Biol. Chem. (1957) 233:171–177.
Buttin and Kornberg, J. Biol. Chem. (1966) 241-54-19–5427.
Brutlag, D. and Kornberg, A., J. Biol. Chem. (1972) 247:241–248.
Chang, L. M. S., J. Biol. Chem (1977) 252:1873–1880.
Chien, A. et al., J. Bacteriol. (1976) 127:1550–1557.
Kaledin, et al., Biokhymiya (1980) 45:644–651 (Russian Text) English translation—Biochem 45(4):494–501.
Lawyer, et al., J. Biol. Chem. (1989) 264:11, pp. 6427–6437.
Bernad, et al., Cell (1989) 59:219.
Neuner, et al., ARch. Microbiol. 153:205–207 (1990).

*Primary Examiner*—David M. Naff
*Assistant Examiner*—Jon P. Weber
*Attorney, Agent, or Firm*—David S. Resnick; David G. Conlin; Gregory D. Williams

[57] ABSTRACT

There is provided an extremely thermostable enzyme obtainable from *Thermococcus litoralis*. The thermostable enzyme has a molecular weight of about 90,000–95,000 daltons, a half-life of about 60 minutes at 100° C. in the absence of stabilizer, and a half-life of about 95 minutes at 100° C. in the presence of stabilizer, such as octoxynol (TRITON X-100) or bovine serum albumin. The thermostable enzyme possesses a 3'-5' proofreading exonuclease activity. The thermostable enzyme may be native or recombinant and may be used for second-strand cDNA synthesis in cDNA cloning, DNA sequencing, and DNA amplification.

7 Claims, 5 Drawing Sheets

LANE 1: MOLECULAR WEIGHT MARKERS
LANE 2: PURIFIED T. litoralis DNA POLYMERASE

PURIFIED THERMOSTABLE DNA POLYMERASE OBTAINABLE FROM THERMOCOCCUS LITORALIS

FIELD OF THE INVENTION

The present invention relates to an extremely thermostable enzyme. More specifically, it relates to a thermostable DNA polymerase obtainable from *Thermococcus litoralis*.

BACKGROUND OF THE INVENTION

DNA polymerases are a family of enzymes involved in DNA repair and replication. Extensive research has been conducted on the isolation of DNA polymerases from mesophilic microorganisms such as *E. coli*. See, for example, Bessman, et al., *J. Biol. Chem.* (1957) 233:171-177 and Buttin and Kornberg *J. Biol. Chem.* (1966) 241:5419-5427.

Examples of DNA polymerases isolated from *E. coli* include *E. coli* DNA polymerase I, Klenow fragment of *E. coli* DNA polymerase I and T4 DNA polymerase. These enzymes have a variety of uses in recombinant DNA technology including, for example, labelling of DNA by nick translation, second-strand cDNA synthesis in cDNA cloning, and DNA sequencing. See Maniatis, et al., *Molecular Cloning: A Laboratory Manual* (1982). Recently, U.S. Pat. Nos. 4,683,195, 4,683,202 and 4,800,159 disclosed the use of the above enzymes in a process for amplifying, detecting, and/or cloning nucleic acid sequences. This process, commonly referred to as polymerase chain reaction (PCR), involves the use of a polymerase, primers and nucleotide triphosphates to amplify existing nucleic acid sequences.

The DNA polymerases discussed above possess a 3'-5' exonuclease activity which provides a proofreading function that gives DNA replication much higher fidelity than it would have if synthesis were the result of only a one base-pairing selection step. Brutlag, D. and Kornberg, A., *J. Biol. Chem.*, (1972) 247:241-248. DNA polymerases with 3'-5' proofreading exonuclease activity have a substantially lower base incorporation error rate when compared with a non-proofreading exonuclease-possessing polymerase. Chang, L. M. S., *J. Biol. Chem.*, (1977) 252:1873-1880.

Research has also been conducted on the isolation and purification of DNA polymerases from thermophiles, such as *Thermus aquaticus*. Chien, A., et al. *J. Bacteriol.* (1976) 127:1550-1557, discloses the isolation and purification of a DNA polymerase with a temperature optimum of 80° C. from *T. aquaticus* YT1 strain. The Chien, et al., purification procedure involves a four-step process. These steps involve preparation of crude extract, DEAE-Sephadex chromatography, phosphocellulose chromatography, and chromatography on DNA cellulose. Kaledin, et al., *Biokhymiya* (1980) 45:644-651 also discloses the isolation and purification of a DNA polymerase from cells of *T. aquaticus* YT1 strain. The Kaledin, et al. purification procedure involves a six-step process. These steps involve isolation of crude extract, ammonium sulfate precipitation, DEAE-cellulose chromatography, fractionation on hydroxyapatite, fractionation on DEAE-cellulose, and chromatography on single-strand DNA-cellulose.

U.S. Pat. No. 4,889,818 discloses a purified thermostable DNA polymerase from *T. aquaticus*, Taq polymerase, having a molecular weight of about 86,000 to 90,000 daltons prepared by a process substantially identical to the process of Kaledin with the addition of the substitution of a phosphocellulose chromatography step in lieu of chromatography on single-strand DNA-cellulose. In addition, European Patent Application 0258017 discloses Taq polymerase as the preferred enzyme for use the PCR process discussed above.

Research has indicated that while the Taq DNA polymerase has a 5'-3' polymerase-dependent exonuclease function, the Taq DNA polymerase does not possess a 3'-5' proofreading exonuclease function Lawyer, F. C., et al. *J. Biol. Chem.*, (1989) 264:11, p. 6427-6437. Bernad, A., et al. *Cell* (1989) 59:219. As a result, Taq DNA polymerase is prone to base incorporation errors, making its use in certain applications undesirable. For example, attempting to clone an amplified gene is problematic since any one copy of the gene may contain an error due to a random misincorporation event. Depending on where in the replication cycle that error occurs (e.g., in an early replication cycle), the entire DNA amplified could contain the erroneously incorporated base, thus, giving rise to a mutated gene product. Furthermore, research has indicated that Taq DNA polymerase has a thermal stability of not more than several minutes at 100° C.

Accordingly, there is a desire in the art to obtain and produce a purified, highly thermostable DNA polymerase with 3'-5' proofreading exonuclease activity, that may be used to improve the DNA polymerase processes described above.

SUMMARY OF THE INVENTION

In accordance with the present invention, there is provided a thermostable enzyme obtainable from *T. litoralis* which catalyzes the polymerization of DNA. The thermostable enzyme obtainable from *T. litoralis* is a DNA polymerase which has an apparent molecular weight of about 90,000-95,000 daltons, a half-life of about 60 minutes at 100° C. in the absence of a stabilizer, and a half-life of about 95 minutes at 100° C. in the presence of a stabilizer such as octoxynol (TRITON X-100) or bovine serum albumin.

The DNA encoding the 90,000-95,000 daltons thermostable DNA polymerase obtainable from *T. litoralis* has been isolated and provides another means to obtain the thermostable enzyme of the present invention.

The *T. litoralis* DNA polymerase possesses 3'-5' proofreading exonuclease activity. This is the first instance of an extreme thermophilic polymerase possessing this proofreading activity. As a result, *T. litoralis* DNA polymerase has a much higher fidelity than a thermostable polymerase with no 3'-5' proofreading exonuclease function, such as Taq polymerase. In addition, the *T. litoralis* DNA polymerase has a substantially greater thermal stability or half life at temperatures from 96° C. to 100° C. than the Taq polymerase. Finally, when used in DNA replication such as the above-described PCR reaction, the *T. litoralis* DNA polymerase is superior to Taq polymerase at amplifying smaller amounts of target DNA in fewer cycle numbers.

DETAILED DESCRIPTION OF THE PREFERRED EMBODIMENTS

The preferred thermostable enzyme herein is a DNA polymerase obtainable from *T. litoralis* strain NS-C (DSM No. 5473). *T. litoralis* was isolated from a submarine thermal vent near Naples, Italy in 1985. This organism, *T. litoralis*, is an extremely thermophilic, sulfur metabolizing, archaebacteria, with a growth range between 55° C. and 98° C. Neuner, et al., *Arch. Microbiol.* (1990) 153:205-207. A sample of *T. litoralis* was deposited with the American Type Culture Collection (ATCC) on Sep. 17, 1991 and has received Accession No. 55233.

For recovering the native protein, *T. litoralis* may be grown using any suitable technique, such as the technique described by Belkin, et al., *Arch. Microbiol.* (1985) 142:181-186, the disclosure of which is incorporated by reference.

Strain NS-C was routinely grown in 2216 marine broth diluted to ½ strength in synthetic seawater (Turks Island Salts, Merck, 1976). For some of the studies, an artificial seawater medium (ASW) was used, as described by Ruby, et. al. (1981). In both cases, a vitamin mix (thiamine-HCl, biotin and $B_{12}$, 40 µg ml$^{-1}$ each), resazurin (0.8 mg l$^{-1}$) and Pipes buffer (20 mM, pH 7.2) were added.

Liquid medium (10 ml, with or without sulfur or organic compounds) was placed in Hungate tubes and flushed for 10 min. with $N_2$. Na-thioglycolate was then injected to make a 0.02% solution, and the tubes were preincubated at 88° C. After approximately 1 h, during which the resazurin turned colorless, the medium was inoculated (to $10^6$ cells ml$^{-1}$ with an 18-24 h culture) and the tubes were incubated at 88° C. without shaking. Steam-autoclaved (110° C.) sulfur, when used, was added in 100 mg amounts to 10 ml medium.

After cell growth, one preferred method for isolation and purification of the enzyme is accomplished using the multi-step process as follows.

First, the cells, if frozen, are thawed, suspended in a suitable buffer such as buffer A (10 mM KPO4 buffer, pH 7.4; 1.0 mM EDTA, 1.0 mM beta-mercaptoethanol), sonicated and centrifuged. The supernatant is then passed through a column which has a high affinity for proteins that bind to nucleic acids such as Affigel blue column (Biorad). The nucleic acids present in supernatant solution of *T. litoralis* and many of the proteins pass through the column and are thereby removed by washing the column with several column volumes of low salt buffer at pH of about 7.0. After washing, the enzyme is eluted with a linear gradient such as 0.1 to 2.0 M NaCl buffer A. The peak DNA polymerase activity is dialyzed and applied to phosphocellulose column. The column is washed and the enzyme activity eluted with a linear gradient such as 0.1 to 1.0 M NaCl in buffer A. The peak DNA polymerase activity is dialyzed and applied to a DNA cellulose column. The column is washed and DNA polymerase activity is eluted with a linear gradient of 0.1 to 1.0 M NaCl in buffer A. The fractions containing DNA polymerase activity are pooled, dialyzed against buffer A, and applied to a high performance liquid chromatography column (HPLC) mono-Q column (anion exchanger). The enzyme is again eluted with a linear gradient such as 0.05 to 1.0 M NaCl in a buffer A. The fractions having thermostable polymerase activity are pooled, diluted and applied to HPLC mono-S column (cation exchanger). The enzyme is again eluted with a linear gradient such as 0.05 to 1.0 M NaCl in buffer A. The enzyme is about 50% pure at this stage. The enzyme may further be purified by precipitation of a contaminating lower molecular weight protein by repeated dialysis against buffer A supplemented with 50 mM NaCl.

The apparent molecular weight of the DNA polymerase obtainable from *T. litoralis* is between about 90,000 to 95,000 daltons when compared with protein standards of known molecular weight, such as phosphorylase B assigned a molecular weight of 97,400 daltons. It should be understood, however, that as a protein from an extreme thermophile, *T. litoralis* DNA polymerase may electrophorese at an aberrant relative molecular weight due to failure to completely denature or other instrinsic properties. The exact molecular weight of the thermostable enzyme of the present invention may be determined from the coding sequence of the *T. litoralis* DNA polymerase gene. The molecular weight of the eluted product may be determined by any technique, for example, by SDS-polyacrylamide gel electrophoresis (SDS-PAGE) using protein molecular weight markers.

Polymerase activity is preferably measured by the incorporation of radioactively labeled deoxynucleotides into DNAse-treated, or activated, DNA; following subsequent separation of the unincorporated deoxynucleotides from the DNA substrate, polymerase activity is proportional to the amount of radioactivity in the acid-insoluble fraction comprising the DNA. Lehman, I. R., et al., *J. Biol. Chem.* (1958) 233:163, the disclosure of which is incorporated herein by reference.

The half-life of the DNA polymerase of the present invention at 100° C. is about 60 minutes. The thermal stability or half-life of the DNA polymerase is determined by preincubating the enzyme at the temperature of interest in the presence of all assay components (buffer, $MgCl_2$, deoxynucleotides, and activated DNA) except the single radioactively-labeled deoxynucleotide. At predetermined time intervals, ranging from 4-180 minutes, small aliquots are removed, and assayed for polymerase activity using the method described above.

The half-life at 100° C. of the DNA polymerase can also be determined in the presence of stabilizers such as the nonionic detergent octoxynol, commonly known as TRITON X-100 (Rohm & Haas Co.), or the protein bovine serum albumin (BSA) or gelatin. The non-ionic detergents polyoxyethylated (20) sorbitan monolaurate (Tween 20, ICI Americas Inc.) and ethoxylated alkyl Phenol (nonyl) (ICONOL NP-40, BASF Wyandotte Corp.) can also be used. Stabilizers are used to prevent the small amount of enzyme added to the reaction mixture from adhering to the sides of the tube or from changing its structural conformation in some manner that decreases its enzymatic activity. The half-life at 100° C. of the DNA polymerase obtainable from *T.*

*litoralis* in the presence of the stabilizer TRITON X-100 or BSA is about 95 minutes.

The thermostable enzyme of this invention may also be produced by recombinant DNA techniques, as the gene encoding this enzyme has been cloned from *T. litoralis* genomic DNA. The complete coding sequence for the *T. litoralis* DNA polymerase can be derived from bacteriophage NEB 619 on an approximately 14 kb BamHI restriction fragment. This phage was deposited with the American Type Culture Collection (ATCC) on Apr. 24, 1990 and has Accession No. ATCC No. 40795. Alternatively, the gene can be constructed by ligating an approximately 1.3 kb Eco RI restriction fragment from bacteriophage NEB 618 (ATCC No. 40794 deposited Apr. 24, 1990), to an approximately 1.6 kb Eco RI fragment isolated from bacteriophage NEB 620 (ATCC No. 40796 deposited Apr. 24, 1990) and an approximately 1.9 kb Eco RI fragment isolated from plasmid NEB 621 (ATCC No. 40797 deposited Apr. 24, 1990). The approximately 1.3 kb Eco RI restriction fragment from NEB 618 comprises the amino-terminal encoding region of the *T. litoralis* DNA polymerase gene while the approximately 1.6 kb Eco RI restriction fragment from NEB 620 and possibly the approximately 1.9 kb Eco RI fragment from NEB 621 comprise the carboxyl-terminus encoding region. Thus, ligation of these three fragments into a correspondingly digested vector will result in the formation of the full *T. litoralis* DNA polymerase gene.

The production of a recombinant form of *T. litoralis* DNA polymerase generally includes the following steps: DNA is isolated which encodes the active form of the polymerase, either in its native form or as a fusion with other sequences which may or may not be cleaved away from the native form of the polymerase and which may or may not effect polymerase activity. Next, the gene is operably linked to appropriate control sequences for expression in either prokaryotic or eukaryotic host/vector systems. The vector preferably encodes all functions required for transformation and maintenance in a suitable host, and may encode selectable markers and/or control sequences for *T. litoralis* polymerase expression. Active recombinant thermostable polymerase can be produced by transformed host cultures either continuously or after induction of expression. Active thermostable polymerase can be recovered either from within host cells or from the culture media if the protein is secreted through the cell membrane.

While each of the above steps can be accomplished in a number of ways, it has been found in accordance with the present invention that for cloning the DNA encoding *T. litoralis* DNA polymerase, [evidence indicates that the] expression of the polymerase from its own control sequences in *E. coli* results in instability of the polymerase gene, high frequency of mutation in the polymerase gene, slow cell growth, and some degree of cell mortality. Therefore, *T. litoralis* thermostable polymerase expression must be tightly controlled in *E. coli* during cloning and expression. Vectors useful in practicing the present invention should provide varying degrees of controlled expression of *T. litoralis* polymerase by providing some or all of the following control features: (1) promoters or sites of initiation of transcription, either directly adjacent to the start of the polymerase or as fusion proteins, (2) operators which could be used to turn gene expression on or off, (3) ribosome binding sites for improved translation, and (4) transcription or translation termination sites for improved stability. Appropriate vectors used in cloning and expression of *T. litoralis* polymerase include, for example, phage and plasmids. Example of phage include lambda gtll (Promega), lambda Dash (Stratagene) lambda ZapII (Stratagene). Examples of plasmids include pBR322, pBluescript (Stratagene), pSP73 (Promega), pGW7 (ATCC No. 40166) and pET3A (Rosenberg, et al., *Gene*, (1987) 56:125–135).

Transformation and Infection

Standard protocols exist for transformation, phage infection and cell culture. Maniatis, et al., *Molecular Cloning: A Laboratory Manual* (1982). Of the numerous *E. coli* strains which can be used for plasmid transformation, the preferred strains include JM101 (ATCC No. 33876), XL1 (Stratagene), and RRI (ATCC No. 31343). *E. coli* strain XL1, ER1578 and ER1458 (Raleigh, et al., *N.A. Research* (1988) 16:1563–1575) are among the strains that can be used for lambda phage, and Y1089 can be used for lambda gtll lysogeny. When preparing transient lysogens in Y1089 (Arasu, et al., *Experimental Parasitology* (1987) 64:281–289), a culture is infected with lambda gtll recombinant phage either by a single large dose of phage or by co-culturing with a lytic host. The infected Y1089 cells are preferably grown at 37° C. in the presence of the inducer IPTG resulting in buildup of recombinant protein within the lysis-defective host/phage system.

Construction of Genomic DNA Expression Library and Screening for Thermostable Polymerase The most common methods of screening for a gene of choice are (1) by hybridization to homologous genes from other organisms, (2) selection of activity by complementation of a host defect, (3) reactivity with specific antibodies, or (4) screening for enzyme activity. Antibody detection is preferred since it initially only requires expression of a portion of the enzyme, not the complete active enzyme. The instability of the *T. litoralis* polymerase gene in *E. coli* would have made success by other methods more difficult.

*T. litoralis* DNA can be used to construct genomic libraries as either random fragments or restriction enzyme fragments. The latter approach is preferred. Preferably, Eco RI partials are prepared from *T. litoralis* genomic DNA using standard DNA restriction techniques such as described in Maniatis, et al., *Molecular Cloning: A Laboratory Manual* (1982), the disclosure of which is incorporated herein by reference. Other restriction enzymes such as BamHI, NruI and XbaI can also be used.

Although methods are available to screen both plasmids and phage using antibodies (Young and Davis, *PNAS*, (1983) 80:1194–1198), in accordance with the present invention it has been found that phage systems tend to work better and are therefore preferred for the first libraries. Since it is uncertain whether *T. litoralis* control regions function in *E. coli*, phage vectors which supply all necessary expression control regions such as lambda gtll and lambda Zap II, are preferred. By cloning *T. litoralis* DNA into the Eco RI site of lambda gt11, *T. litoralis* polymerase may be expressed either as a fusion protein with beta-galactosidase or from its own endogenous promoter.

Once formed, the expression libraries are screened with mouse anti- *T. litoralis* DNA polymerase antiserum using standard antibody plaque hybridization procedures such as those described by Young and Davis, *PNAS* (1983), supra.

The mouse anti-*T. litoralis* DNA polymerase antiserum used to screen the expression libraries can be prepared using standard techniques, such as the techniques described in Harlow and Cane, *Antibodies: A Laboratory Manual* (1988) CSH Press, the disclosure of which is incorporated herein by reference. Since most sera react with *E. coli* proteins, it is preferable that the *T. litoralis* polymerase antisera be preabsorbed by standard methods against *E. coli* proteins to reduce background reactivity when screening expression libraries. Phage reacting with anti-*T. litoralis* polymerase antiserum are picked and plaque purified. Young and Davis, *PNAS* (1983), supra.

The *T. litoralis* DNA polymerase DNA, coding for part of the whole gene, can then be subcloned in, for example, pBR322, pBluescript, M13 or pUC19. If desired, the DNA sequence can be determined by, for example, the Sanger dideoxy chain-terminating method (Sanger, F., Nicklen, S. & Coulson, A. R. *PNAS* (1977) 74:5463–5467).

Identification of DNA Encoding and Expression of the *T. litoralis* DNA Polymerase Several methods exist for determining that the DNA sequence coding for the *T. litoralis* DNA polymerase has been obtained. These include, for example, comparing the amino-terminal sequence of the protein produced by the recombinant DNA to the native protein, or determining whether the recombinant DNA produces a protein which binds antibody specific for native *T. litoralis* DNA polymerase. In addition, research by Wang, et al., *FASEB Journal* (1989) 3:20 suggests that certain regions of DNA polymerase sequences are highly conserved among many species. As a result, by comparing the predicted amino acid sequence of the cloned gene with the amino acid sequence of known DNA polymerases, such as human DNA polymerase and *E. coli* phage T4 DNA polymerase, the identification of these islands of homology provides strong evidence that the recombinant DNA indeed encodes a DNA polymerase.

Once identified, the DNA sequence coding for the *T. litoralis* DNA polymerase, can be cloned into an appropriate expression vector such as a plasmid derived from *E. coli*, for example, pET3A, pBluescript or pUC19, the plasmids derived from the *Bacillus subtilis* such as pUB110, pTP5 and pC194, plasmids derived from yeast such as pSH19 and pSH15, bacteriophage such as lambda phage, bacteria such as *Agrobacterium tumefaciens*, animal viruses such as retroviruses and insect viruses such as Baculovirus.

Overexpression of the *T. litoralis* DNA polymerase can be achieved, for example, by separating the *T. litoralis* DNA polymerase gene from its endogenous control elements and then operably linking the polymerase gene to a very tightly controlled promoter such as a T7 expression vector. See, Rosenberg, et al., *Gene* (1987) 56:125–135, which is hereby incorporated by reference. Insertion of the strong promoter may be accomplished by identifying convenient restriction targets near both ends of the *T. litoralis* DNA polymerase gene and compatible restriction targets on the vector near the promoter, and transferring the *T. litoralis* DNA polymerase gene into the vector in such an orientation as to be under transcriptional and translational control of the strong promoter.

*T. litoralis* DNA polymerase may also be overexpressed by utilizing a strong ribosome binding site placed upstream of the *T. litoralis* DNA polymerase gene to increase expression of the gene. See, Shine and Dalgarno, *Proc. Natl. Acad. Sci. USA* (1974) 71:1342–1346, which is hereby incorporated by reference.

The recombinant vector is introduced into the appropriate host using standard techniques for transformation and phage infection. For example, the calcium chloride method, as described by Cohen, S. N., *PNAS* (1972)) 69:2110 is used for *E. coli*, the disclosure of which is incorporated by reference. The transformation of Bacillus is carried out according to the method of Chang, S., et al., *Molecular and General Genetics* (1979) 168:111, the disclosure of which is incorporated by reference. Transformation of yeast is carried out according to the method of Parent, et al., *Yeast* (1985) 1:83–138, the disclosure of which is incorporated by reference. Certain plant cells can be transformed with *Agrobacterium tumefaciens*, according to the method described by Shaw, C. H., et al., Gene (1983) 23:315, the disclosure of which is incorporated by reference. Transformation of animal cells is carried out according to, for example, the method described in *Virology* (1973) 52:456, the disclosure of which is incorporated by reference. Transformation of insect cells with Baculovirus is carried out according to, for example, the method described in Biotechnology (1988) 6:47, the disclosure of which is incorporated herein by reference.

The transformants are cultivated, depending on the host cell used, using standard techniques appropriate to such cells. For example, for cultivating *E. coli*, cells are grown in LB media (Maniatis, supra) at 30° C. to 42° C. to mid log or stationary phase.

The *T. litoralis* DNA polymerase can be isolated and purified from a culture of transformed host cells, for example, by either extraction from cultured cells or the culture solution.

When the *T. litoralis* DNA polymerase is to be extracted from a cultured cell, the cells are collected after cultivation by methods known in the art, for example, centrifugation. Then, the collected cells are suspended in an appropriate buffer solution and disrupted by ultrasonic treatment, lysozyme and/or freeze-thawing. A crude extract containing the *T. litoralis* DNA polymerase is obtained by centrifugation and/or filtration.

When the *T. litoralis* DNA polymerase is secreted into the culture solution, i.e., alone or as a fusion protein with a secreted protein such as maltose binding protein, the supernatant is separated from the cells by methods known in the art.

The separation and purification of the *T. litoralis* DNA polymerase contained in the culture supernatant or the cell extract can be performed by the method described above, or by appropriate combinations of known separating and purifying methods. These methods include, for example, methods utilizing solubility such as salt precipitation and solvent precipitation, methods utilizing the difference in molecular weight such as dialysis, ultra-filtration, gel-filtration, and SDS-polyacrylamide gel electrophoresis, methods utilizing a difference in electric charge such as ion-exchange column chromatography, methods utilizing specific affinity such as affinity chromatography, methods utilizing a difference in hydrophobicity such reverse-phase high performance liquid chromatography and methods utilizing a difference in isoelectric point such as isoelectric focusing electrophoresis.

Stabilization and Use of the *T. litoralis* DNA Polymerase

For long-term storage, the thermostable enzyme of the present invention is stored in the following buffer: 0.05 M NaCl, 0.01 M KPO$_4$ (pH 7.4), 0.1 mM EDTA and 50% glycerol at −20° C.

The *T. litoralis* DNA polymerase of the present invention may be used for any purpose in which such an enzyme is necessary or desirable. For example, in recombinant DNA technology including, second-strand cDNA synthesis in cDNA cloning, and DNA sequencing. See Maniatis, et al., supra.

The *T. litoralis* DNA polymerase of the present invention may be modified chemically or genetically to inactivate the 3'-5' exonuclease function and used for any purpose in which such a modified enzyme is desirable, e.g., DNA sequencing.

For example, genetically modified *T. litoralis* DNA polymerase may be isolated by randomly mutagenizing the *T. litoralis* DNA polymerase gene and then screening for those mutants that have lost exonuclease activity, without loss of polymerase activity. Alternatively, genetically modified *T. litoralis* DNA polymerase may be isolated using the site-directed mutagenesis technique described in Kunkel, T. A., *PNAS* (1985) 82:488–492, the disclosure of which is herein incorporated by reference.

In addition, the *T. litoralis* DNA polymerase of the present invention may also be used to amplify DNA, e.g., by the procedure disclosed in U.S. Pat. Nos. 4,683,195, 4,683,202 and 4,800,159.

The following examples are given to illustrate embodiments of the present invention as it is presently preferred to practice. It will be understood that the examples are illustrative, and that the invention is not to be considered as restricted except as indicated in the appended claims.

EXAMPLE 1

Purification of a Thermostable DNA Polymerase From *Thermococcus Litoralis*

*Thermococcus litoralis* strain NS-C (DSM No. 5473) was grown in the media described by Belkin, et al. supra, containing 10 g/l of elemental sulfur in a 100 liter fermentor at its maximal sustainable temperature of approximately 80° C. for two days. The cells were cooled to room temperature, separated from unused sulfur by decanting and collected by centrifugation and stored at −70° C. The yield of cells was 0.8 g per liter.

183 g of cells obtained as described above, were suspended in 550 ml of buffer A (10 mM KPO$_4$ buffer, pH 7.4; 1.0 mM EDTA, 1.0 mM beta-mercaptoethanol) containing 0.1 M NaCl and sonicated for 5 minutes at 4° C. The lysate was centrifuged at 15,000 g for 30 minutes at 4° C. The supernatant solution was passed through a 470 ml Affigel blue column (Biorad). The column was then washed with 1000 ml of buffer A containing 0.1 M NaCl. The column was eluted with a 2000 ml linear gradient from 0.1 to 2.0 M NaCl in buffer A. The DNA polymerase eluted as a single peak at approximately 1.3 M NaCl and represented 80% of the activity applied. The peak activity of DNA polymerase (435 ml) was dialyzed against 4 liters of buffer A, and then applied to 80 ml Phosphocellulose column, equilibrated with buffer A containing 0.1 M NaCl. The column was washed with 160 ml of buffer A containing 0.1 M NaCl, and the enzyme activity was eluted with 1000 ml linear gradient of 0.1 to 1.0 M NaCl in buffer A. The activity eluted as a single peak at 0.6 M NaCl and represented 74% of the activity applied. The pooled activity (150 ml) was dialyzed against 900 ml of buffer A and applied to a 42 ml DNA-cellulose column. The column was washed with 84 ml of buffer A containing 0.1 M NaCl, and the enzyme activity eluted with a linear gradient of buffer A from 0.1 to 1.0 M NaCl. The DNA polymerase activity eluted as a single peak at 0.3 M NaCl, and represented 80% of the activity applied. The activity was pooled (93 ml). The pooled fractions were dialyzed against 2 liters of buffer A containing 0.05 M NaCl and then applied to a 1.0 ml HPLC mono-Q column (Pharmacia). The DNA polymerase activity was eluted with a 100 ml linear gradient of 0.05 M to 1.0 M NaCl in buffer A. The DNA polymerase activity eluted as a single peak at 0.1 M NaCl and represented 16% of the activity applied. The pooled fractions (3.0 ml) were diluted to 6 ml with buffer A and applied to an 1.0 ml HPLC mono-S column (Pharmacia) and eluted with a 100 ml linear gradient in buffer A from 0.05 to 1.0 M NaCl. The activity eluted as a single peak at 0.19 M NaCl and represented 75% of the activity applied.

Figure 1A:
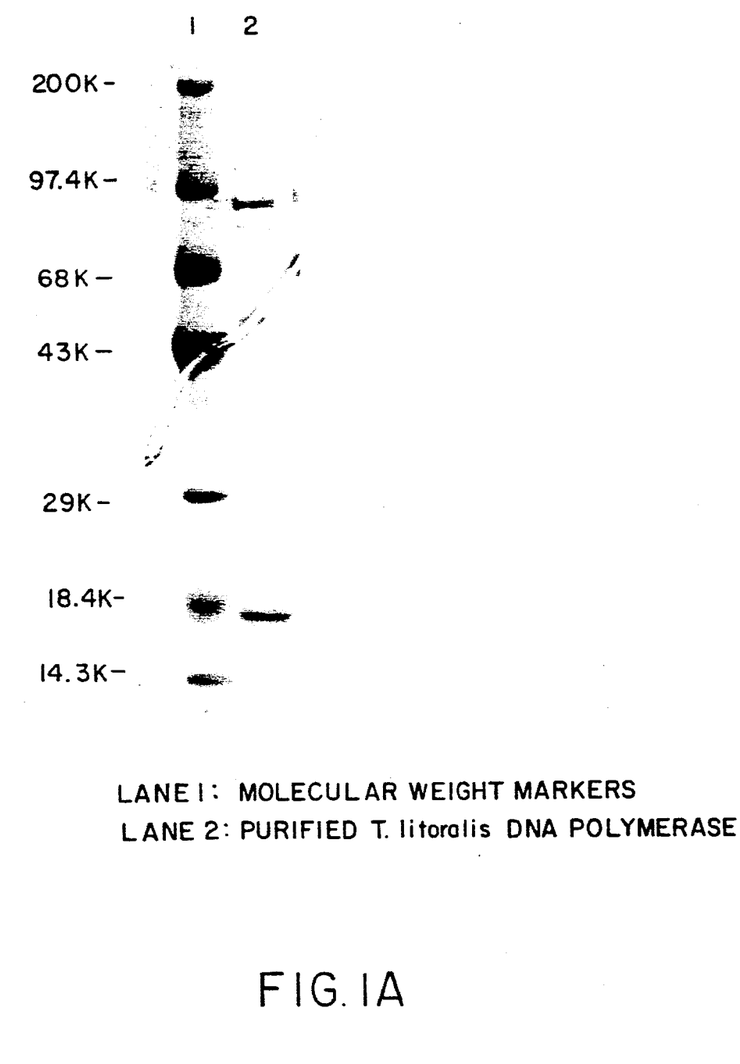
FIG. 1A—is a photograph of the SDS-polyacrylamide gel of example 1.
Figure 1B:
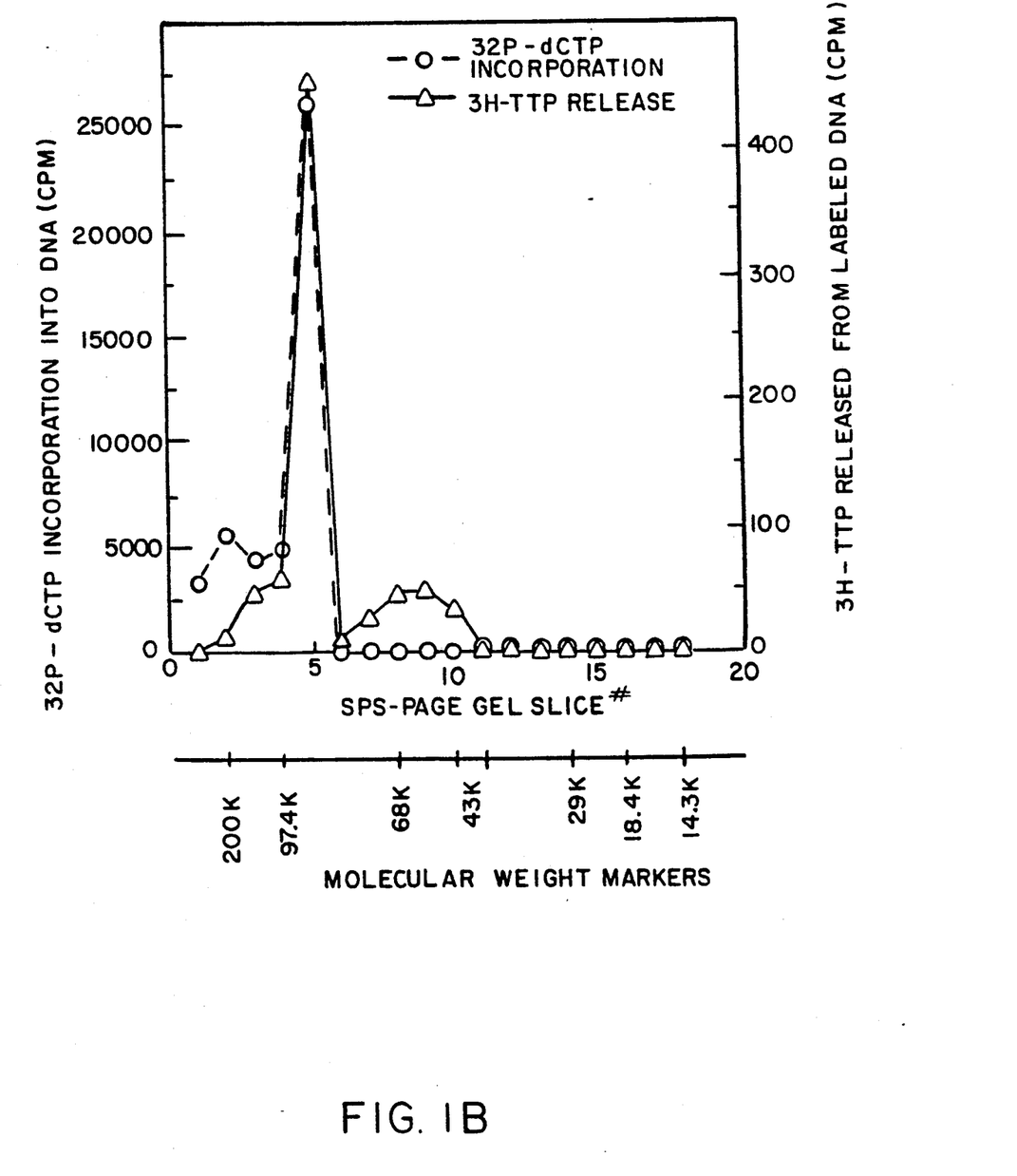
FIG. 1B—is a graph showing the polymerase activity and exonuclease activity of the proteins eluted from lane 2 of the gel in FIG. 1A.

By SDS-polyacrylamide gel electrophoresis (SDS-PAGE) and subsequent staining of the proteins using a colloidal stain (ISS Problue) more sensitive than Coomassie Blue. (Neuhoff, et al., *Electrophoresis* (1988) 9:255–262), it was determined that the DNA polymerase preparation was approximately 50% pure: two major bands were present, one at 90,000 to 95,000 daltons and a doublet at 18,000 daltons. FIG. 1A. A very minor band was evident at approximately 80,000 to 85,000 daltons. At this level of purification the polymerase had a specific activity of 300,000 units of polymerase activity per mg of polymerase protein. On a separate SDS-polyacrylamide gel verification of the identity of the stained band at 90,000 to 95,000 daltons was obtained by cutting the gel lane containing the purified *T. litoralis* polymerase into 18 slices. Embedded proteins were eluted from the gel by crushing the gel slices in a buffer containing 0.1% SDS and 100 μg/ml BSA. The eluted proteins were denatured by exposure to guanidine HCl, then renatured via dilution of the denaturant as described by Hager and Burgess *Analytical Biochemistry* (1980) 109:76–86. Polymerase activity as measured by incorporation of radioactivity labeled $^{32}$P-dCTP into acid-insoluble DNA (as previously described) and assayed for exonuclease activity (as measured by the release of $^3$H-labelled DNA to an acid soluble form as described in Example V). As shown in FIG. 1B, only the 90,000 to 95,000 daltons band alone showed either significant polymerase activity or exonuclease activity.

The DNA polymerase preparation was dialyzed against buffer A containing 0.05 M NaCl. As was determined by SDS-PAGE, much of the 18,000 dalton protein precipitated out of the solution. The yield of *T. litoralis* DNA polymerase was determined to be 0.5 mg by quantitative protein analysis, and this represented 6.5% of the total activity present in the starting crude extract.

Purified *T. litoralis* polymerase was electrophoresed and stained with either Coomassie Blue or the colloidal stain (ISS Problue) previously described to detect protein. One deeply staining protein band was seen at about 90,000 to 95,000 daltons; this molecular weight determination was obtained by comparison on the same gel to the migration of the following marker proteins (Bethesda Research Laboratories): myosin, 200,000 daltons; phosphorylase B, 97,400 daltons; BSA, 68,000 daltons; ovalbumin, 43,000 daltons, carbonic anhydrase 29,000 daltons; b-lactoglobulin, 18,400 daltons; lysoyzme 14,300 daltons.

EXAMPLE II

Cloning of T. Litoralis DNA Polymerase Gene

A. Production of Mouse Anti-T. Litoralis DNA Polymerase Antiserum

Immunization of Mice

A 3 ml solution containing 0.4 mg of polymerase protein (obtained by the method of Example I) was concentrated at 4° C. to approximately 0.3 ml and used to inoculate two mice. The purified T. litoralis polymerase preparation consisted of four bands of approximately 85–95, 75–85, and a doublet of 10–25 kDal on Coomassie blue stained SDS-PAGE gels. As shown in Example I, the T. litoralis polymerase is approximately 90–95 kDal. Both T. litoralis polymerase antisera recognize all four proteins present in the immunogen.

The immunization schedule was as follows: mouse one was immunized intraperitioneally (IP) with 20 μg of T. litoralis polymerase, prepared as above, in Freunds' complete adjuvant (FCA). Seven days later, both mice were immunized IP with 50 μg T. litoralis polymerase in FCA. Twenty-seven days later both mice were immunized IP with 30 μg T. litoralis polymerase for mouse one and 50 μg T. litoralis polymerase for mouse two in Freunds' incomplete adjuvant. Mouse one was bled two weeks later and mouse two was bled 20 days later. Sera was prepared from blood by standard methods (Harlow and Lane, *Antibodies: A Laboratory Manual*, 1988).

Anti-T. litoralis polymerase antisera was diluted in TBSTT (20 mM Tris pH 7.5, 150 mM NaCl, 0.2% Tween 20, and 0.05% Triton-X 100) containing 1% BSA, 0.1% NaAzide, 0.1% PMSF.

Preabsorption of Anti-T. litoralis Polymerase Antiserum Against E. coli lysates Since most sera react with E. coli proteins, T. litoralis polymerase antisera were preabsorbed, using the following method, against E. coli proteins to reduce background reactivity when screening libraries or recombinant antigens. E. coli cell paste was thawed and lysed by sonication and soluble protein was bound to Affigel 10 (Biorad) as described by the manufacturer. 4 ml of E. coli resin were washed two times in TBS (TBSTT without detergents). 0.35 ml of sera was diluted approximately 1 to 5 in TBSTT, 1% BSA, 0.1% NaAzide and mixed with resin overnight at 4° C. The resin was pelleted by centrifugation and washed. The recovered preabsorbed sera was at a 1 to 17 dilution and was stored frozen at −20° C. until use.

For screening, preabsorbed sera was diluted as above to a final concentration of 1:200.

B. Identification of a Probe For The T. litoralis Polymerase Gene

Construction of a lambda qtll Expression Library

A probe for the T. litoralis polymerase gene was obtained following immunological screening of a lambda gtll expression library.

T. litoralis DNA was partially digested as follows: four μg of T. litoralis DNA was digested at 37° C. with five units of Eco RI in a 40 μl reaction using Eco RI buffer (Eco RI buffer=50 mM NaCl, 100 mM Tris pH 7.5, 20 mM MgCl$_2$, 10 mM BME). Three μl of 100 mM EDTA was added to 15 μl samples at 30, 45 and 60 minutes. 2 μg of T. litoralis DNA was digested for 90 minutes at 37° C. with 20 units of Eco RI in 20 μreaction using Eco RI buffer and the reaction was stopped by adding 2 μl of 100 mM EDTA. 0.2 μg of each digest was electrophoresed on an agarose gel to monitor the extent of digestion. Approximately 3 μg of T. litoralis DNA Eco RI partials (14 μl from the 60-minute digest and 19 μl from the 90-minute digest) were pooled to form the "Eco RI pool" and heated at 65° C. for 15 minutes.

0.5 μl of the Eco RI pool were ligated to 0.28 μg of Eco RI cut, bacterial alkaline phosphatase treated lambda gtll DNA in a five μl reaction using standard ligation buffer (ligation buffer=66 mM Tris pH 7.5, 1 mM ATP, 1 mM spermidine, 10 mM MgCl2, 15 mM DTT, and 2 mg/ml gelatin) and 0.5 μl T4 DNA ligase (New England Biolabs No. 202). The ligation was performed at 16° C. overnight. 4 μl of this ligation reaction were packaged using Gigapack Gold (Stratagene) according to the manufacturers instructions. After incubation at room temperature for two hours, the packaged phage were diluted in 500 μl of SM (SM=100 mM NaCl, 8 mM MgSO$_4$, 50 mM Tris pH 7.5, 0.01% gelatin) plus three drops chloroform. The packaged Eco RI library was called sample V6-1 and consisted of $1.1 \times 10^5$ individual phage. E. coli strain ER1578 was used for phage infection.

Immunological Screening of Lambda gtll Expression Library

The initial phage library was screened (Young, R. A. and R. W. Davis Science. (1983) 222:778–782) with a 1:200-dilution of the antiserum produced above. 36 phage (V10-22 through V10-55) which reacted with the anti-T. litoralis DNA polymerase antiserum were picked and 16 phage were plaque purified.

The 16 antibody positive phage were used to lysogenize E. coli K-12 strain Y1089. Lysogens were screened for thermostable DNA polymerase activity, no activity was detected.

Western blots (Towbin, et al., *PNAS*, (1979) 76:4350–4354) from these 16 lysates were probed with anti-T. litoralis polymerase antiserum. All proteins from these lysates which reacted with T. litoralis polymerase antiserum were smaller than T. litoralis polymerase, and were also smaller than beta-galactosidase, indicating that none were fusion proteins with beta-galactosidase.

Eight of the 16 antibody positive phage were used to affinity purify epitope-specific antibodies from total antiserum (Beall and Mitchell, *J. Immunological Methods*, (1986) 86:217–223).

The eight affinity purified sera were used to probe Western blots of both purified T. litoralis polymerase and T. litoralis crude lysates. Antibody purified from NEB 618 plaques specifically reacted with T. litoralis polymerase in purified and T. litoralis crude lysates. This was strong evidence that phage NEB 618 encodes approximately 38 kDal of the amino terminus of the T. litoralis polymerase.

Characterization of Phage NEB 618 and Subcloning of Eco RI Inserts

Western blot analysis indicated that phage NEB 618 synthesized several peptides ranging in size from approximately 15-40 kDal which bound *T. litoralis* polymerase antisera. DNA from phage NEB 618 was purified from liquid culture by standard procedures (Maniatis, et al., supra.) Digestion of NEB 618 DNA with Eco RI yielded fragments of 1.3 and 1.7 kb. An Eco RI digest of NEB 618 DNA was ligated to Eco RI cut pBluescript DNA. 20 μg of pBluescriptSK+ were digested with 40 units of Eco RI in 40 μl Eco RI buffer at 37° C. for three hours, followed by 65° for 15 minutes. 10 μg of NEB 618 DNA were digested with 40 units of Eco RI in 40 μl Eco RI buffer at 37° C. for 75 minutes, followed by 65° C. for 15 minutes. 1.75 μg of Eco RI cut NEB 618 DNA were ligated to 20 ng Eco RI cut pBluescriptSK+ with one μl T4 DNA ligase (New England Biolabs No. 202) in 10 μl ligation buffer. The ligation was performed overnight at 16° C. JM101 CaCl competent cells (Maniatis, et al., supra) were transformed with 5 μl of the ligation mixture. Of 24 recombinants examined, all but one contained the 1.7 kb fragment; clone V27-5.4 contained the 1.3 kb *T. litoralis* DNA fragment.

Antibodies from *T. litoralis* polymerase mouse antisera were affinity purified, as described above, on lysates from V27-5.4 (encoding the 1.3 kb Eco RI fragment) and V27-5.7 (encoding the 1.7 kb Eco RI fragment in pBluescript) and reacted with Western blot strips containing either purified or crude *T. litoralis* polymerase. Antibodies selected on lysates of V27-5.4 reacted with *T. litoralis* polymerase in both crude and purified preparations. In addition, the first three amino acids from the N-terminal protein sequence of native *T. litoralis* polymerase (methionine-isoleucine-leucine) are the same as in the predicted open reading frame (ORF) in the V27-5.4 clone.

From these results it was concluded that V27-5.4 encoded the amino terminal of *T. litoralis* polymerase. The insert DNA was large enough to encode the biggest peptides synthesized by this clone, but not the entire *T. litoralis* polymerase.

Construction and Screening of *T. litoralis* Secondary Libraries

Antibody screening discussed above, had identified the DNA fragment coding the amino terminal half of the *T. litoralis* polymerase. In order to find a fragment large enough to code for the entire gene, restriction digests of *T. litoralis* DNA were probed with the amino terminal half of the polymerase gene contained in clone V27-5.4. Restriction digests were performed in separate tubes using a master mix which contained 1.2 μg of *T. litoralis* DNA in 39 μl of restriction enzyme buffer (REB, restriction enzyme buffer=50 mM NaCl, 10 mM Tris pH 7.5, 20 mM MgCl2, 10 mM BME), to which 1.5-200 U of enzyme were added as followed: 1.5 U AvrII, 9 U EaeI, 10 U NheI, 20 U NotI, 9 U SpeI, 20 U XhoI, 30 U XbaI, 20 U SacI, 10 U BamHI, 20 U ClaI, 20 U HindIII, 20 U PstI, 12 U NaeI, 10 U ScaI, 12 U XmnI, 20 U EcoRV, 20 U Sal, 20 U Eco RI, 200 U EagI, 20 U DraI, 5 U HapI, 8 U NruI, 4 U SnaBI, 8 U StuI, 10 U BclI, 8 U BglII, 10 U RsaI, 10 U HaeIII, 8 U AluI, 4 U HincII, 10 U PvuII, 6 U SspI. One μl 10 mg/ml BSA was added to the HincII digest. BalI digest was prepared as above except there was 0 mM NaCl in the buffer. All digests were overnight at 37° C. except BclI which was incubated at 50° C. Digests were electrophoresed on agarose gels and transferred to NC (Southern, *J. Mol. Biol.* (1975) 98:503-517). The filters were probed with radiolabeled V27-5.4 DNA and hybridization was detected by autoradiography. In most digests, V27-5.4 DNA hybridized to fragments greater than 20 kb, except BamHI (approximately 14 kb), Eco RI (1.3 kb), HindIII (approximately 2.4, 5.4 kb), XbaI (approximately 8 kb), ClaI (approximately 4.4, 5.5 kb), BalI (approximately 8.5 kb), HincII (approximately 2.1, approximately 2.4 kb), NruI (approximately 5.5 kb), BglII (approximately 2.9 kb), HaeIII (approximately 1.3, approximately 1.4 kb) and RsaI which gave numerous small bands.

Digests yielding single fragments large enough to encode the entire polymerase gene, estimated to be 2.4-3 kb, based on the size of the native protein, were BamHI, XbaI, and NruI.

BamHI Library

A BamHI genomic library was constructed using lambda DashII. Lambda DashII is a BamHI substitution vector that can be used to clone 10-20 kb BamHI DNA fragments. 25-75 nanograms of *T. litoralis* genomic DNA digested with BamHI, as described above, was ligated to 0.5 μg BamHI digested, calf intestine phosphatase treated lambda DashII DNA in five μl of standard ligation buffer including 0.5 μl T4 DNA ligase (New England Biolabs No. 202). Three μl of the ligation reaction was packaged (Gigapack Plus, Stratagene) as described above. Plaque lifts of 8,000 plaques from the lambda DashII library were probed with labeled gel purified 1.3 kb Eco RI fragment from clone V27-5.4 (Maniatis, et al., supra). 2.5% of the phage hybridized to the 1.3 kb Eco RI DNA fragment, two of which were plaque purified (clones lambda NEB 619 and lambda V56-9). Both phage contained a 12-15 kb BamHI fragment which hybridized to the 1.3 kb Eco RI fragment and contained the approximately 8 kb XbaI and approximately 5.5 kb NruI fragments. The BamHI insert was subcloned into pBR322. Colonies containing this fragment grew very poorly and, based on the polymerase assay described above, failed to produce detectable levels of thermostable DNA polymerase.

XbaI Library

*T. litoralis* DNA digested with XbaI was cloned into the XbaI site of pUC19. Colony lifts were probed with radiolabeled V27-5.4 DNA. No positive clones were detected.

Figure 2:
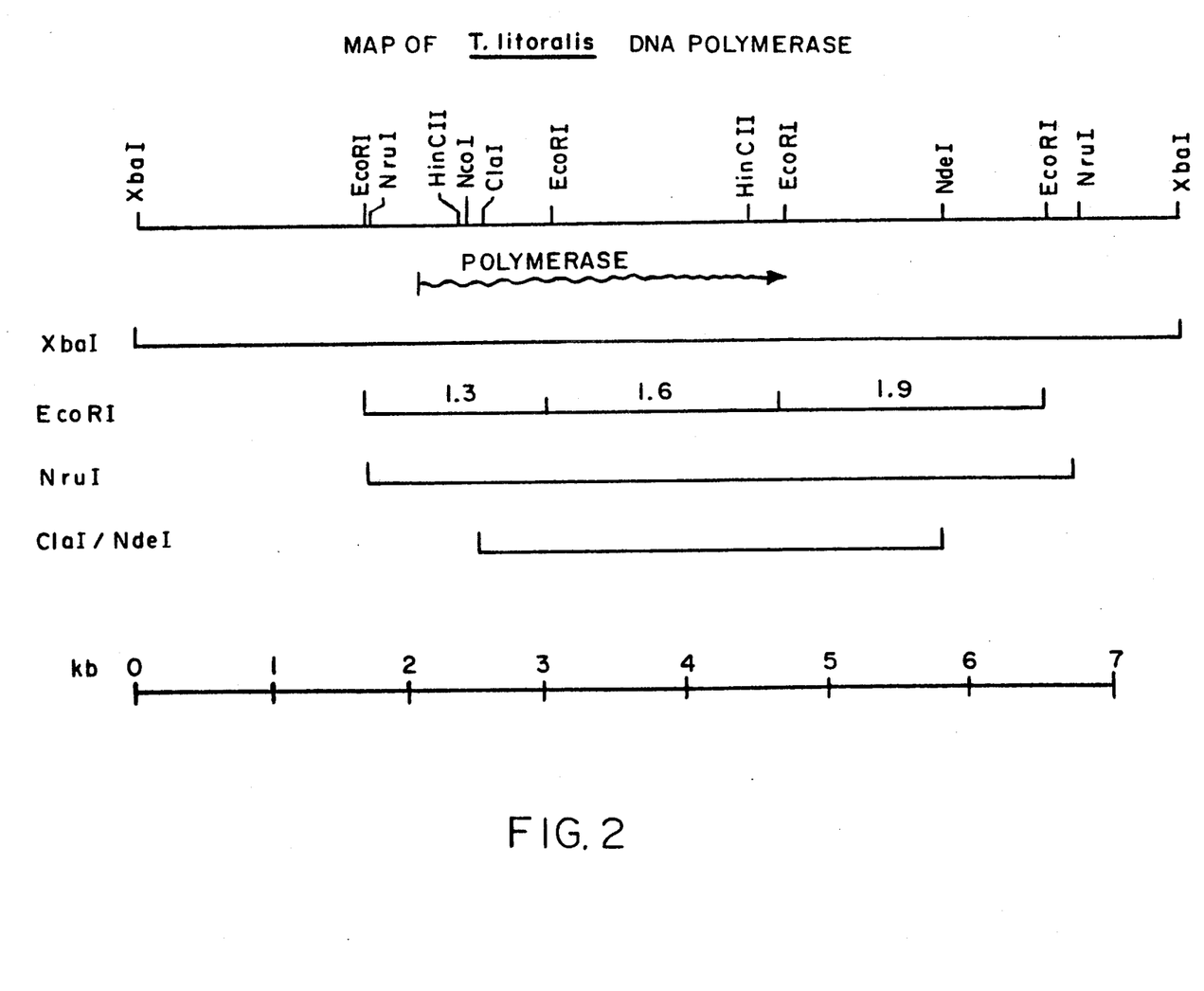
FIG. 2—is a restriction site map of the Xba fragment containing the gene encoding the *T. litoralis* DNA Polymerase which is entirely contained within the BamHI fragment of bacteriophage NEB 619.

The XbaI fragment from the BamHI insert in lambda NEB 619 (BamHI library above) was subcloned into the XbaI site of pUC19. Approximately 0.3 μg of NEB 619 DNA digested with BamHI was ligated to 0.1 μg pUC19 DNA digested with BamHI using two μl T4 DNA ligase (New England Biolabs No. 202) in 20 μl of standard ligation buffer. The ligation was incubated overnight at 16° C. CaCl competent JM101 and XL-1 cells were transformed with five μl of ligation mix and incubated overnight at 37° C. (Maniatis, et al., supra). Colony lifts were probed with radiolabeled purified 1.3 kb Eco RI fragment from V27-5.4 DNA. No positives were detected. Competent RRI cells were transformed with 10 μl of ligation mix and incubated overnight at 30° C. Micro-colonies were picked and mini-plasmid preparations (boiling method, Maniatis, et al., supra) analyzed. Most of these clones contained the approximately 8 kb XbaI fragment. The rationale for this latter experiment was that since the BamHI clones grew poorly, there would be an increased chance of isolating a plasmid containing the *T. litoralis* polymerase gene from an XbaI colony that also grew slowly. Also, lower temperature of incubation results in less copies of pUC19 plasmids per cell. These results provided evidence that the *T. litoralis* polymerase gene was toxic to *E. coli*. Using the polymerase activity assay described above, no thermostable polymerase activity was detected in these clones. Restriction analysis indicated that the XbaI clones should contain the entire polymerase gene. See FIG. 2.

NruI Libraries

Approximately 0.3 μg of NEB 619 DNA (BamHI library above) cut with NruI was ligated to 0.1 μg of pUC19 DNA cut with HincII exactly as described for the XbaI library. Again, no positives were found by hybridization when cells were incubated at 37° C., but when transformants were incubated at 30° C., many micro-colonies were observed. The majority of these micro-colonies contained the approximately 5.5 kb NruI insert. Using the polymerase activity assay described above, no thermostable polymerase activity was detected in these colonies. Analysis of these colonies determined that when the direction of *T. litoralis* polymerase transcription was the same as lacZ in pUC19, the colonies failed to grow at 37° C. and were extremely unstable. However, colonies in which the direction of *T. litoralis* polymerase transcription was opposite of lacZ in pUC19, such as in clone Nru21, were more stable. This indicated that transcription of *T. litoralis* polymerase is detrimental to *E. coli*, and may explain why it was so difficult to clone the entire gene. Restriction mapping analysis indicated that the NruI clones should contain the entire polymerase gene. See FIG. 2.

Conclusions Concerning Direct Cloning of the Polymerase

The *T. litoralis* is approximately 90–95 kDal which would require approximately 2.4–3.0 kb DNA to encode the entire gene. Restriction mapping analysis of the 1.3 kb Eco RI fragment, coding for the amino-terminus of the *T. litoralis* polymerase gene, found within the BamHI, XbaI and NruI clones, discussed above, indicates that all three clones contain the entire polymerase gene. All of these larger clones were unstable in *E. coli*. Therefore, alternate methods, as discussed below, for cloning the polymerase were tested.

D. Cloning the Second Half of *T. litoralis* Polymerase Gene

It is believed that when the entire *T. litoralis* polymerase gene was cloned in *E. coli* while under its endogenous control, mutations in the gene arose. To prevent selection of inactive mutants, the polymerase gene was cloned from the *T. litoralis* genome in 2 or more pieces which should each separably be inactive and therefore not selected against. Restriction mapping of the *T. litoralis* genome was used to determine which restriction enzymes would produce fragments that would be appropriate for cloning the second half of the *T. litoralis* polymerase gene. Although the above data indicates that expression of *T. litoralis* polymerase was toxic for *E. coli*, it was also possible that DNA sequences themselves, in or outside of the coding region, were toxic. Therefore, the minimum sized fragment which could encode the entire gene was determined to be the best choice. Restriction analysis indicated that there was an approximately 1.6 kb Eco RI fragment adjacent to the 3' end of the amino terminal 1.3 kb Eco RI fragment (see FIG. 2) which could possibly complete the polymerase gene.

Hybridization probe for the second half of the *T. litoralis* DNA polymerase gene Since none of the previous clones expressed thermostable polymerase activity, it was possible that they had accumulated mutations in the coding sequence and would therefore not be suitable sources of the second half of the gene. Hybridization probes were therefore required in order to clone the downstream fragments from the genome. The approximately 3.2 kb NdeI/ClaI fragment from clone Nru21 (the Nru21 clone contains an approximately 5.5 kb insert, beginning approximately 300 bp upstream from the start of the polymerase gene) was subcloned into pSP73 (Promega) creating clone NC11. CaCl competent RRI cells were transformed, as above, with the ligation mixture. Mini-plasmid preps of transformants were analyzed by digestion with NdeI and ClaI and clone NC11 containing the *T. litoralis* 3.2 kb NdeI/ClaI fragment was identified. This clone was stable in *E. coli*. The pNC11 insert was sequenced (Sanger, et al., *PNAS*, (1977) 74:5463–5467). The ClaI end was identical to the pV27-5.4 sequence (1.3 kb Eco RI fragment coding for the amino-terminus of the *T. litoralis* polymerase). The 1.3 kb Eco RI junction and beyond was sequenced using primers derived from the 1.3 kb Eco RI fragment sequence. The NdeI end was sequenced from primers within the vector.

Screening of Eco RI Genomic Libraries

10 μg of pNC11 were digested with 30 U of Eco RI in 100 μl of Eco RI buffer at 37° C. for two hours. The approximately 1.6 kb Eco RI fragment was purified on DE-81 paper (Whatman) after electrophoresis. The approximately 1.6 kb Eco RI fragment was radiolabeled and used to probe the original Eco RI lambda gt11 library. Infection and plaque lifts were performed as above. Three positives were identified and plaque purified. All contain the approximately 1.6 kb Eco RI fragment, but some also contain other inserts.

An Eco RI library was also constructed in lambda ZapII. 2 μg of *T. litoralis* DNA were digested with 20 U Eco RI for five hours at 37° C. in 20 μl Eco RI buffer and then heat treated at 65° C. for 15 minutes. Approximately 15 nanograms of *T. litoralis* DNA/Eco RI was ligated to 0.5 μg of Eco RI cut, phosphatased lambda ZapII DNA (Stratagene) with 0.5 μl T4 DNA ligase (New England Biolabs No. 202) in 5 μl of ligation buffer at 16° C. overnight. 4 μl of ligated DNA was packaged (GigaPack Gold, Stratagene). Infection and plaque lifts were performed as above. Approximately 1,500 phage were probed with radiolabeled approximately 1.6 kb Eco RI fragment as above. Five hybridization positive plaques were picked and three were plaque purified. Two phage (NEB 620 and V109-2) were rescued as pBluescript recombinants (V117-1 and V117-2) by in vivo excision according to the manufacturer's instructions (Stratagene). Both contained the approximately 1.6 kb Eco RI fragment plus different second fragments. The 5' end was sequenced and corresponds to the sequence determined from NC11 (ClaI/NdeI fragment). See FIG. 2. This Eco RI fragment contains 3/6 of the T4 DNA polymerase family homology islands as described by Wang, et al., supra.

The sequence of the 1.6 kb Eco RI and ClaI/NdeI fragments indicated that the 1.9 kb Eco RI fragment may be necessary to complete the polymerase gene. Lambda ZapII phage, V110-1 through V110-7, containing the 1.9 kb Eco RI fragment were identified as described above for NEB 620 using labeled probes. The approximate 1.9 kb Eco RI fragment from a lambda gt11 phage was subcloned into the Eco RI site of pACYC 184 creating plasmid NEB 621.

The entire *T. litoralis* polymerase gene has been cloned as BamHI, XbaI and NruI fragments which were unstable and from which the active enzyme was not detected. The gene has also been cloned in three pieces (1.3 kb Eco RI fragment, approximately 1.6 kb Eco RI fragment and approximately 1.9 kb Eco RI fragment) which are large enough to encode all of the *T. litoralis* DNA polymerase gene. The 1.3 kb Eco RI fragment stably expresses the amino terminal portion of the polymerase.

EXAMPLE III

Over-Expression of the *Thermococcus Litoralis* DNA Polymerase Gene

The gene fragments obtained in Example II may be used in a number of approaches, or combinations thereof, to obtain maximum expression of the cloned *T. litoralis* DNA polymerase.

One such approach comprises separating the *T. litoralis* DNA polymerase gene from its endogenous control elements and then operably linking the polymerase gene to a very tightly controlled promoter such as a T7 expression vector (Rosenberg, et al., *Gene* (1987) 56:125-135). Insertion of the strong promoter may be accomplished by identifying convenient restriction targets near both ends of the *T. litoralis* DNA polymerase gene and compatible restriction targets on the vector near the promoter, and transferring the *T. litoralis* DNA polymerase gene into the vector in such an orientation as to be under transcriptional and translational control of the strong promoter.

*T. litoralis* DNA polymerase may also be expressed by cloning the enzyme in *E. coli* strains with temperature-sensitive DNA polymerases and selecting for complementation of this lack of host DNA polymerase activity Bryan, S. and Moses, R. E., J. Bacteriology (1988) 170:456.

*T. litoralis* DNA polymerase may also be overexpressed by utilizing a strong ribosome binding site placed upstream of the *T. litoralis* DNA polymerase gene to increase expression of the gene. See, Shine and Dalgarno, *Proc. Natl. Acad. Sci. USA* (1974) 71:1342-1346, which is hereby incorporated by reference.

Another approach for increasing expression of the *T. litoralis* DNA polymerase gene comprises altering the DNA sequence of the gene by site directed mutagenesis or resynthesis to contain initiation codons that are more efficiently utilized than *E. coli.*

A further approach for increasing the expression of *T. litoralis* DNA polymerase gene comprises designing oligonucleotide primers for hybridization to both sides of the *T. litoralis* DNA polymerase gene based on DNA sequence, to take advantage of the DNA polymerase chain reaction to amplify the DNA polymerase gene. The amplified fragment is inserted into an expression vector such as pGW7 (ATCC No. 40166) or pET3A from William Studier, (Brookhaven, Nat. Lab., Upton, N.Y.). Both vectors contain a strong promoter and a ribosome binding site. Even strongly regulated promoters may be subject to read through expression, to limit this possibility transcription terminator sequences can be placed just upstream of the controlled promoter. Also, an inducible antisense promoter can be placed 3' to the end of the polymerase gene to reduce read through transcription.

An amber mutation can be introduced into the *T. litoralis* DNA polymerase gene allowing cloning in *E. coli* by preventing expression in hosts which lack amber suppressors.

Finally, *T. litoralis* DNA polymerase may be more stable in eukaryote systems like yeast and Baculovirus.

The *T. litoralis* DNA polymerase may be produced from clones carrying the *T. litoralis* DNA polymerase gene by propagation in a fermentor in a rich medium containing appropriate antibiotics. Cells are thereafter harvested by centrifugation and disrupted by sonication to produce a crude cell extract containing the *T. litoralis* DNA polymerase activity.

The crude extract containing the *T. litoralis* DNA polymerase activity is purified by the method described in Example I, or by standard product purification techniques such as affinity-chromatography, or ion-exchange chromatography.

EXAMPLE IV

*T. Litoralis* DNA Polymerase Half-Life Determination

The thermostability or half-life of the *T. litoralis* DNA polymerase purified as described above in Example 1 was determined by the following method. Purified *T. litoralis* DNA polymerase (25 units) was preincubated at 100° C. in the following buffer: 70 mM tris-HCl (pH 8.8 at 25° C.), 17 mM ammonium sulfate, 7 mM MgCl$_2$, 10 mM beta-mercaptoethanol, 200 $\mu$M each deoxynucleotide and 200 $\mu$g/ml DNAse-treated DNA. An initial sample was taken at time zero and a small aliquot equivalent to 5% of the enzyme mixture was removed at 10, 20, 40, 60, 90, 120, 150, and 180 minutes. The polymerase activity was measured by determining incorporation of deoxynucleotide into DNA as described previously.

A sample of Taq DNA polymerase obtained from New England Biolabs was subjected to the above assay. An initial sample was taken at time zero and a small aliquot equivalent to 5% of the enzyme mixture was removed at 4, 7, and 10 minutes. As shown in the FIG. 3, the half-life of the *T. litoralis* DNA polymerase at 100° C. was 60 minutes, while the half-life of the Taq polymerase at 100° C. was 4.5 minutes.

Figure 3:
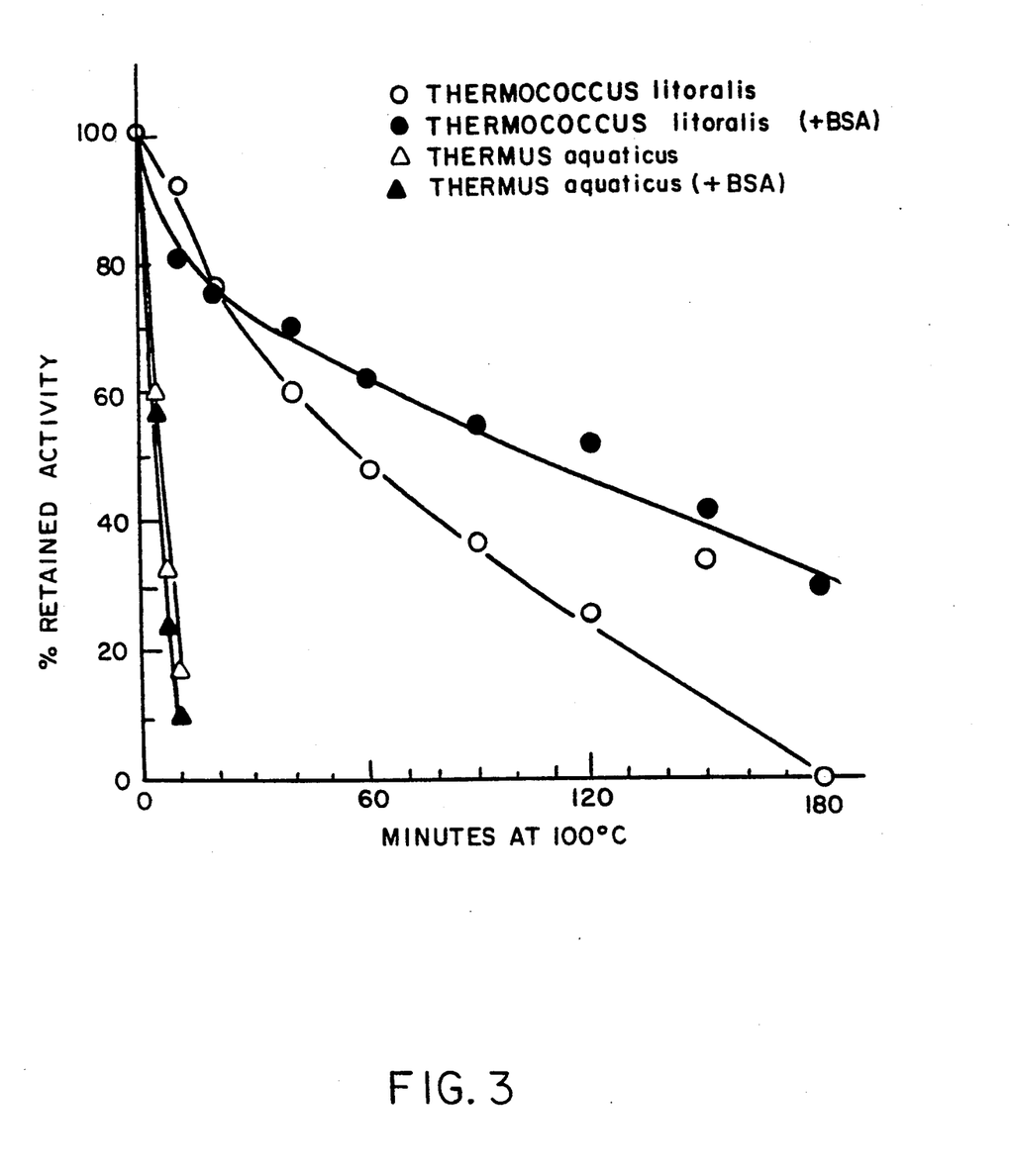
FIG. 3—is a graph showing the half-life of the *T. litoralis* DNA polymerase and the Taq DNA polymerase at 100° C.

As shown in FIG. 3, the half-life of *T. litoralis* DNA polymerase at 100° C. in the absence of stabilizers was 60 minutes, while in the presence of the stabilizers TRITON X-100 (0.15%) or BSA (100 $\mu$g/ml) the half-life was 95 minutes. This was in stark contrast to the half-life of Taq DNA polymerases at 100° C., which in the presence or absence of stabilizers was 4.5 minutes (FIG. 3).

EXAMPLE V

Determination of 3'-5' Proofreading Activity

1. Response of *T. litoralis* DNA Polymerase to the Absence or Presence of Deoxynucleotides The levels of exonuclease activities associated with polymerases show very different responses to deoxynucleotides. Nonproofreading 5'-3' exonucleases are stimulated tenfold or greater by concomitant polymerization afforded by the presence of deoxynucleotides, while proofreading 3'-5' exonucleases are inhibited completely by concomitant polymerization. Lehman, I. R. ARB (1967) 36:645.

The *T. litoralis* DNA polymerase or polymerases with well-characterized exonuclease functions (T4 Polymerase, Klenow fragment) were incubated with 1 μg $^3$H-thymidine-labeled double-stranded DNA ($10^5$ CPM/μg) in polymerization buffer (70 mM tris (pH 8.8 at 24° C.), 2 mM MgCl2, 0.1% Triton and 100 μg/ml bovine serum albumin). After an incubation period of three hours (experiment 1) or four hours (experiment 2) at either 70° C. (thermophilic polymerases) or 37° C. (mesophilic polymerases), the exonuclease-hydrolyzed bases were quantified by measuring the acid-soluble radioactively-labeled bases.

As shown in Table 1, the Taq DNA polymerase, with its 5'-3' exonuclease activity, shows stimulation of exonuclease activity when deoxynucleotides were present at 30 uM. However, polymerases with 3'-5' proofreading exonuclease activities, such as the T4 polymerase, Klenow fragment of *E. coli* polymerase I, or the *T. litoralis* DNA polymerase showed the reverse, an inhibitory response to the presence of deoxynucleotides.

polymerase, which contains a well-characterized 3'-5' proofreading exonuclease activity, are very similar.

2. Response of *T. litoralis* DNA Polymerase to Increasing Deoxynucleotide Concentrations Exonuclease activities of polymerases are affected by the level of deoxynucleotides present during polymerization, in as much as these levels affect polymerization. As deoxynucleotide levels are increased towards the Km (Michaelis constant) of the enzyme, the rate of polymerization is increased. For exonuclease functions of polymerases sensitive to the rate of polymerization, changes in exonuclease activity are parallel with increases in deoxynucleotide concentrations. The increase in polymerization rate drastically decreases proofreading 3'-5' exonuclease activity with a concomitant in polymerization-dependent 5'-3' exonuclease activity.

The exonuclease function of the *T. litoralis* DNA polymerase was compared to those of well-characterized exonuclease functions of other polymerases as the deoxynucleotide concentration was increased from 10 uM to 100 uM. The exonuclease activity was measured as described in (1) with an incubation period of 30 minutes. As summarized in Table 2, the *T. litoralis* DNA polymerase responded to increases in deoxynucleotide levels similarly to a polymerase known to possess a 3'-5' proofreading exonuclease (Klenow fragment of *E. coli* DNA Pol. I). This response was in contradiction to that of a polymerase known not to possess this proofreading function, Taq DNA polymerase. This polymerase responded to an increase in deoxynucleotide levels with an increase in exonuclease function due to its 5'-3' exonuclease activity.

TABLE 2

| | | Acid-Soluble CPM (Exonuclease Activity) | | |
|---|---|---|---|---|
| Amount | Type of DNA Polymerase | 10 uM dNTPS | 100 uM dNTPS | Effect on Hydrolysis with Increasing dNTPS |
| 5 units | Taq Polymerase | 350 | 610 | 1.7X increase |
| 5 units | Klenow fragment of *E. coli* Pol. I | 650 | 300 | 2.2X decrease |
| 5 units | *T. litoralis* Polymerase | 180 | 110 | 1.6X decrease |

Figure 4:
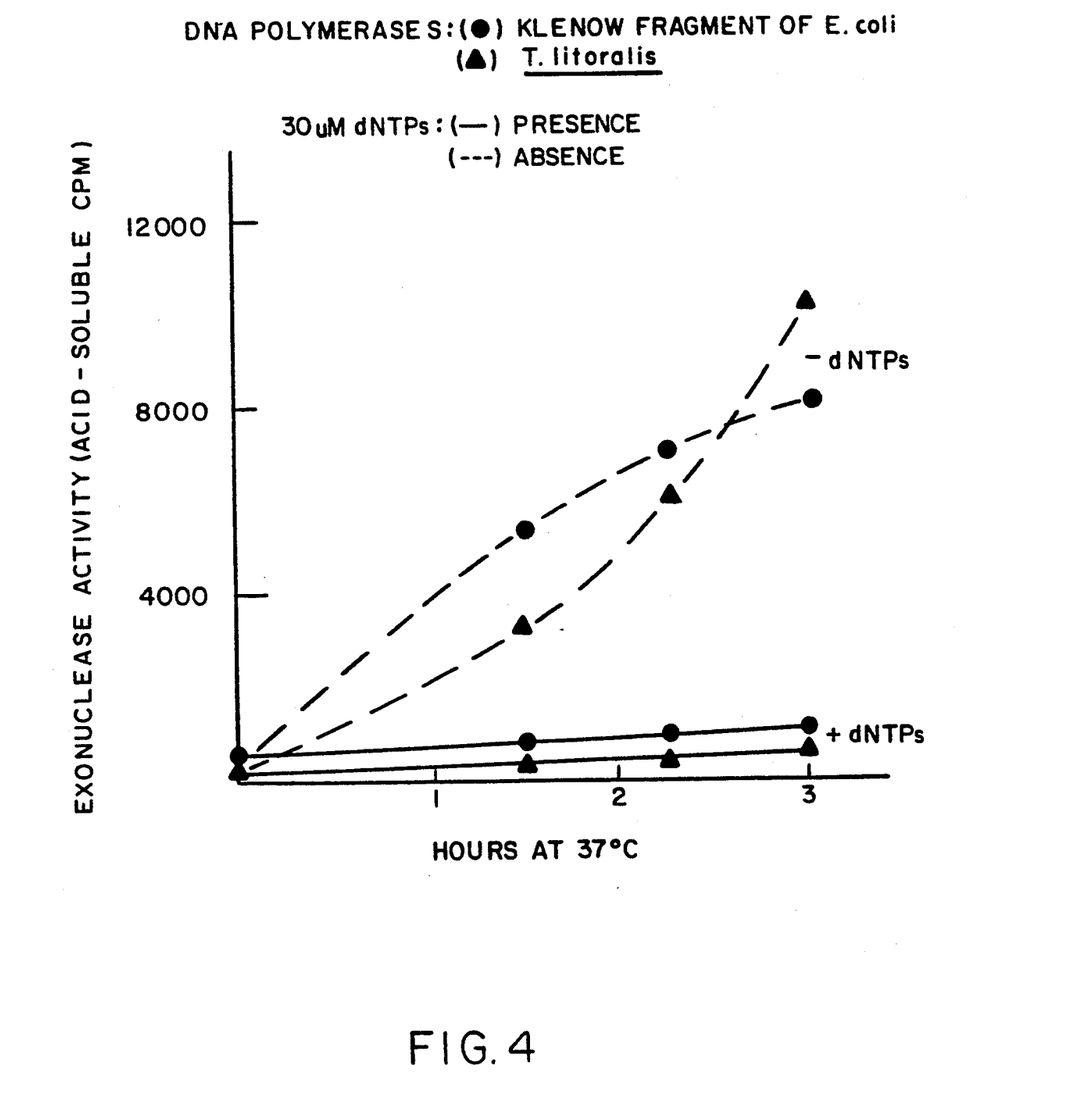
FIG. 4—is a graph showing the response of *T. litoralis* DNA polymerase and Klenow fragment to the presence or absence of deoxynucleotides.

The similarity of responses to the presence or absence of deoxynucleotides of the *T. litoralis* DNA polymerase and the well-characterized Klenow fragment of the *E. coli* DNA polymerase is further shown in FIG. 4. Twenty units of either polymerase was incubated with 9 μg $^3$H-thymidine-labeled double-stranded DNA ($10^5$ CPM/μg) in 350 μl polymerization buffer as described above in the presence, or absence of, 30 μM deoxynucleotides.

3. Response of *T. litoralis* DNA Polymerase to Alteration from a Balanced Deoxynucleotide State to an Unbalanced State Polymerization is dependent on equal levels of all four deoxynucleotides present during DNA synthesis. If the deoxynucleotide levels are not equal, polymerases have decreased polymerization rates and are more likely to insert incorrect bases. Such conditions greatly

TABLE 1

| | | | Acid-Soluble CPM (Exonuclease Activities)* | | |
|---|---|---|---|---|---|
| Experiment # | Amount | Type of DNA Polymerase | no dNTPS | 30 uM dNTPS | Effect Upon Adding NTPS |
| 1 | 2.5 units | Taq Polymerase | 241 | 1936 | 8X increase |
| | 3 units | T4 Polymerase | *47608 | 6663 | 7X decrease |
| | 10 units | Klenow Fragment of *E. coli* Pol. I | 11272 | 2845 | 4X decrease |
| 2 | 5 units | Taq Polymerase | 338 | 2539 | 8X increase |
| | 5 units | T4 Polymerase | *46001 | 10418 | >4X decrease |
| | 5 units | Klenow Fragment of *E. coli* Pol. I | 8757 | 408 | 22X decrease |
| | 5 units | *T. litoralis* Polymerase | 8573 | 795 | 11X decrease |

*Nonlineart range of assay

At each time point, 50 μl was removed and the level of acid-soluble radioactively-labeled bases were measured. As FIG. 4 documents, the behavior of *T. litoralis* DNA polymerase and the Klenow fragment of *E. coli* DNA increase proofreading 3'-5' exonuclease activities while decreasing 5'-3' exonuclease activities. Lehman, I. R., ARB (1967) 36:645

The *T. litoralis* DNA polymerase was incubated with both balanced deoxynucleotide levels (30 uM) and two levels of imbalance characterized by dCTP present at 1/10 or 1/100 the level of the other three deoxynucleotides. The response of the *T. litoralis* DNA polymerase was then compared to that of three polymerases possessing either the 3'-5' or the 5'-3' exonuclease functions. All assays were performed as described in (1) except for dCTP concentrations listed below. As seen in Table 3 below, the *T. litoralis* DNA polymerase follows the expected behavior for a proofreading 3'-5' exonuclease-containing polymerase; an imbalance in deoxynucleotide pools increased the exonuclease activity in a similar manner as that of the proofreading polymerases of T4 DNA polymerase or Klenow fragment of *E. coli* DNA polymerase I. In contrast to this response, the exonuclease of the Taq DNA polymerase was not affected until the imbalance was heightened to the point that polymerization was inhibited.

4. Directionality of Exonuclease Activity

A proofreading exonuclease has a 3'-5' directionality on DNA while nonproofreading exonuclease associated with DNA polymerases have a 5'-3' directionality. To discern the direction of the exonuclease activity of *T. litoralis* DNA polymerase, the 5' blocked DNA of adenovirus was utilized. Since the 5' end of this DNA is blocked by protein, enzymic activities that are 5'-3' in directionality cannot digest this double-stranded DNA; however, enzymic activities that are 3'-5', such as exonuclease III or proofreading exonuclease-containing polymerases, can digest adenovirus DNA.

polymerization-dependent exonuclease activity, showed no disappearance of the DNA fragment.

EXAMPLE VI

Performance of *T. litoralis* DNA Polymerase in the PCR Process

The ability of the *T. litoralis* DNA polymerase to perform the polymerase chain reaction (PCR) was also examined. In 100 μl volumes containing the buffer described in Example IV, varying amounts of M13mp18 DNA cut by ClaI digestion, generating 2 fragments of 4355 bp and 2895 bp, were incubated with 200 ng of calf thymus DNA present as carrier DNA to decrease any nonspecific adsorption effects. The forward and reverse primers were present at 1 μM (forward primer=5'd(-CCAGCAAGGCCGATAGTTTGAGTT)3' and the reverse primer=5' d(CGCCAGGGTTTTCCCAGT-CACGAC)3'). These primers flank a 1 kb DNA sequence on the 4355 bp fragment described above, with the sequence representing 14% of the total M13mp18 DNA. Also present were 200 μM each dNTP, 100 μg/ml BSA, 10% DMSO and 2.5 units of either *T. aquaticus* DNA polymerase (in the presence or absence of 0.5% NP40 and 0.05% Tween 20), or *T. litoralis* DNA polymerase (in the presence or absence of 0.10% Triton X-100). The initial cycle consisted of 5 min at 95° C., 5 min at 50° C. (during which polymerase and BSA additions were made) and 5 min at 70° C. The segments of each subsequent PCR cycle were the following: 1 min at 93° C., 1 min at 50° C. and 5 min at 70° C. After 0, 13, 23 and 40 cycles, 20 μl amounts of 100 μl volumes were removed and subjected to agarose gel electropho-

TABLE 3

| Type of DNA Polymerase (5 units @) | Acid-soluble CPM (Exonuclease Activity) | | | |
| --- | --- | --- | --- | --- |
| | no dNTPS | 30 uM dNTPS | 30 uM/3 uM* | 30 uM/0.3 uM** |
| Taq Polymerase | 338 | 2539 | 2243 | 656 |
| T4 Polymerase | ***46001 | 10418 | ***43850 | ***46585 |
| Klenow Fragment of *E. coli* Pol. I | 8757 | 408 | 1291 | 1755 |
| *T. litoralis* Polymerase | 8573 | 795 | 3471 | 3339 |

*3 uM dCTP, 30 uM all other dNTPs
**0.3 uM dCTP, 30 uM all other dNTPs
***nonlinear range of assay Twenty-five units of exonuclease III or 20 units of either *T. litoralis* DNA polymerase, T4 DNA polymerase (possessing a well characterized 3'-5' exonuclease activity), or Taq DNA polymerase (lacking such an activity) were incubated with 5 μg adenovirus DNA for time periods up to 30 minutes duration at either 37° C. (T4 polymerase and exonuclease III) or 70° C. (Taq polymerase and *T. litoralis* polymerase) in the presence of 70 mM tris-HCl pH 8.8 at 25° C., 2 mM MgCl₂ and 100 μg/ml BSA. At the end of each incubation time period, enzymic activity was stopped by phenol extraction of the adenovirus DNA, followed by HpaI digestion for one hour at 37° C. in 20 mM tris, pH 7.9 at 25° C., 10 mM Magnesium acetate 50 mM potassium acetate and 1 mM DTT. The DNA fragments were subjected to agarose gel electrophoresis and the resulting pattern of time-dependent degradation and subsequent loss of double-stranded DNA fragments were assessed.

The 3'-5' exonuclease activities of exonuclease III, of *T. litoralis* DNA polymerase and T4 DNA polymerase caused the disappearance of the double-strand DNA fragments originating from the 5' blocked end of the adenovirus DNA, indicating vulnerability of its 3' end. In contrast, the Taq DNA polymerase with its 5'-3' resis with ethidium bromide present to quantitate the amplification of the 1 kb DNA sequence.

Initial experiments with this target DNA sequence present at 28 ng and 2.8 ng established the ability of the *T. litoralis* DNA polymerase to catalyze the polymerase chain reaction; yields were comparable or not more than twofold greater than the seen with *T. aquaticus* DNA polymerase.

However, it was at the lower levels of target DNA sequence, 2.8 femtograms, that differences in polymerase function were most apparent. Under these conditions requiring maximal polymerase stability and/or efficiency at elongation of DNA during each cycle, the *T. litoralis* DNA polymerase produced greater than fourfold more amplified DNA than that of *T. aquaticus* DNA polymerase within 23 cycles.

This ability to amplify very small amounts of DNA with fewer cycles is important for many applications of PCR since employing large cycle numbers for amplification is associated with the generation of undesirable artifacts during the PCR process.

We claim:

1. A purified thermostable enzyme obtainable from *Thermococcus litoralis* which catalyzes the polymerization of DNA, wherein said enzyme has a molecular weight of 90,000 to 95,000 daltons, a 3'-5' exonuclease activity and is substantially free of *Thermococcus litoralis* nucleic acid.

2. The thermostable enzyme of claim 1, having a half life of about 60 minutes at 100° C. in the absence of a stabilizer.

3. The thermostable enzyme of claim 1, having a half life of about 95 minutes at 100° C. in the presence of a stabilizer.

4. The thermostable enzyme of claim 3, wherein said stabilizer is a nonionic-detergent.

5. The thermostable enzyme of claim 4, wherein said nonionic-detergent is selected from the group consisting of octoxynol, polyoxyethylated sorbitan monolaurate and ethoxylated nonyl phenol.

6. The thermostable enzyme of claim 3, wherein the stabilizer is a protein selected from the group consisting of Bovine Serum Albumin and gelatin.

7. The polymerase of claim 1, wherein said polymerase is isolated from a recombinant organism transformed with a vector that codes for the expression of *Thermococcus litoralis* DNA polymerase.

* * * * *

UNITED STATES PATENT AND TRADEMARK OFFICE
CERTIFICATE OF CORRECTION

PATENT NO. : 5,210,036

DATED : May 11, 1993

INVENTOR(S) : Comb, et al.

It is certified that error appears in the above-indentified patent and that said Letters Patent is hereby corrected as shown below:

Column 11, line 6, replace "b-lactoglobulin" with --ß-lactoglobulin--

Column 11, lines 6-7, replace "lysozyme" with --lysozyme--

Column 12, line 22, replace "MgCl2" with --MgCl$_2$--

Column 13, line 57, replace "MgCl2" with --MgCl$_2$--

Column 13, line 65, replace "HapI" with --HpaI--

Column 16, lines 62-63, replace "in vivo" with --*in vivo*--

Column 19, line 20, replace "MgCl2" with --MgCl$_2$--

Column 22, line 51, replace "the" with --that--

Signed and Sealed this

Third Day of September, 1996

Attest:

BRUCE LEHMAN

Attesting Officer

Commissioner of Patents and Trademarks